US006902923B1

(12) United States Patent
Walke et al.

(10) Patent No.: US 6,902,923 B1
(45) **Date of Patent: *Jun. 7, 2005**

(54) HUMAN KINASE PROTEINS AND POLYNUCLEOTIDES ENCODING THE SAME

(75) Inventors: D. Wade Walke, Spring, TX (US); John Scoville, Houston, TX (US); Gregory Donoho, Portage, MI (US); C. Alexander Turner, Jr., The Woodlands, TX (US); Brian Mathur, The Woodlands, TX (US); Daniel Mathur, Wooster, OH (US); Carl Johan Friddle, The Woodlands, TX (US)

(73) Assignee: Lexicon Genetics Incorporated, The Woodlands, TX (US)

(*) Notice: Subject to any disclaimer, the term of this patent is extended or adjusted under 35 U.S.C. 154(b) by 88 days.

This patent is subject to a terminal disclaimer.

(21) Appl. No.: 10/306,879

(22) Filed: Nov. 25, 2002

Related U.S. Application Data

(63) Continuation of application No. 09/883,134, filed on Jun. 15, 2001, now Pat. No. 6,511,840.

(60) Provisional application No. 60/216,382, filed on Jul. 7, 2000, and provisional application No. 60/211,572, filed on Jun. 15, 2000.

(51) Int. Cl.[7] ............................ C12N 1/20; C12N 9/20; C12N 15/00; C12N 5/00; C12Q 1/68

(52) U.S. Cl. ................................ 435/252.3; 435/320.1; 435/325; 435/6; 435/194; 536/23.2

(58) Field of Search ........................... 435/252.3, 320.1, 435/194, 325, 6; 536/23.2

(56) References Cited

U.S. PATENT DOCUMENTS

| | | | | |
|---|---|---|---|---|
| 4,215,051 | A | | 7/1980 | Schroeder et al. |
| 4,376,110 | A | | 3/1983 | David et al. |
| 4,594,595 | A | | 6/1986 | Struckman |
| 4,631,211 | A | | 12/1986 | Houghten |
| 4,689,405 | A | | 8/1987 | Frank et al. |
| 4,713,326 | A | | 12/1987 | Dattagupta et al. |
| 4,873,191 | A | | 10/1989 | Wagner et al. |
| 4,946,778 | A | | 8/1990 | Ladner et al. |
| 5,252,743 | A | | 10/1993 | Barrett et al. |
| 5,424,186 | A | | 6/1995 | Fodor et al. |
| 5,445,934 | A | | 8/1995 | Fodor et al. |
| 5,459,127 | A | | 10/1995 | Felgner et al. |
| 5,556,752 | A | | 9/1996 | Lockhart et al. |
| 5,700,637 | A | | 12/1997 | Southern |
| 5,744,305 | A | | 4/1998 | Fodor et al. |
| 5,830,721 | A | | 11/1998 | Stemmer et al. |
| 5,837,458 | A | | 11/1998 | Minshull et al. |
| 5,869,336 | A | | 2/1999 | Meyer et al. |
| 5,877,397 | A | | 3/1999 | Lonberg et al. |
| 5,948,767 | A | | 9/1999 | Scheule et al. |
| 6,001,593 | A | | 12/1999 | Bandman et al. |
| 6,075,181 | A | | 6/2000 | Kucherlapati et al. |
| 6,110,490 | A | | 8/2000 | Thierry |
| 6,150,584 | A | | 11/2000 | Kucherlapati et al. |
| 2003/0211093 | A1 | * | 11/2003 | Yue et al. .................. 424/94.5 |

OTHER PUBLICATIONS

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Gordon, 1989, "Transgenic Animals", International Review of Cytology, 115:171–229.

Greenspan et al, 1993, "Idiotypes: structure and immunogenicity", FASEB Journal 7:437–444.

Gu et al, 1994, "Deletion of a DNA Polymerase β Gene Segment in T Cells Using Cell Type–Specific Gene Targeting", Science 265:103–106.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the lpp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Lakso et al, 1992, "Targeted oncogene activation by site–specific recombination in transgenic mice", Proc. Natl. Acad. Sci. USA 89:6232–6236.

Lavitrano et al, 1989, "Sperm Cells ad Vectors for Introducing Froeign DNA into Eggs: Genetic Transformation of Mice", Cell 57:717–723.

(Continued)

*Primary Examiner*—Maryam Monshipouri

(57) ABSTRACT

Novel human polynucleotide and polypeptide sequences are disclosed that can be used in therapeutic, diagnostic, and pharmacogenomic applications.

2 Claims, No Drawings

OTHER PUBLICATIONS

Lo, 1983, "Transformation by Iontopheric Microinjection of DNA: Multiple Integrations without Tandem Insertions", Mol. & Cell. Biology 3(10):1803–1814.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberg et al., 1984, "Recombinant antibodies possessing novel effector functions," Nature 312:604:608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa californica* Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. USA 82:6148–6152.

Van Heeke et al, 1989, "Expression of Human Asparagine Synthetase in *Escherichia coli*", J. Biol. Chemistry 264:(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

* cited by examiner

HUMAN KINASE PROTEINS AND POLYNUCLEOTIDES ENCODING THE SAME

The present application is a continuation of U.S. application Ser. No. 09/883,134, filed on Jun. 15, 2001, now U.S. Pat. No. 6,511,840 which issued on Jan. 28, 2003, which claims the benefit of U.S. Provisional Application Ser. Nos. 60/211,572 and 60/216,382 which were filed on Jun. 15, 2001 and Jul. 7, 2000, respectively. These Applications are herein incorporated by reference in their entirety.

1. INTRODUCTION

The present invention relates to the discovery, identification, and characterization of novel human polynucleotides encoding a protein that shares sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotides, antagonists and agonists of the proteins, and other compounds that modulate the expression or activity of the proteins encoded by the disclosed polynucleotides that can be used for diagnosis, drug screening, clinical trial monitoring, the treatment of physiological disorders or diseases, and cosmetic or nutriceutical applications.

2. BACKGROUND OF THE INVENTION

Kinases mediate phosphorylation of a wide variety of proteins and compounds in the cell. Along with phosphatases, kinases are involved in a range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal kinases, including, but not limited to myosin kinases and unconventional myosin classes of proteins (SEQ ID NOS:1–5) as well as serine-threonine kinases, calcium/calmodulin-dependent kinases and MAP kinases (SEQ ID NOS:6–11). As such, the novel polynucleotides encode a new kinase protein having homologues and orthologs across a range of phyla and species.

The novel human polynucleotides described herein, encode open reading frames (ORFs) encoding proteins of 238, 1,236, 974, 922 and 255 amino acids in length (see respectively SEQ ID NOS: 2, 4, 7, 9, 11).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described polynucleotide under the control of a strong promoter system), and transgenic animals that express a NHP transgene, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–11 are "knocked-out" they provide a method of identifying phenotypic expression of the particular gene as well as a method of assigning function to previously unknown genes. Additionally, the unique NHP sequences described in SEQ ID NOS:1–11 are useful for the identification of coding sequence, the identification of the actual biologically relevant exon splice junctions and the mapping of a unique gene to a particular chromosome.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human kinase proteins. SEQ ID NO:5 describes a full length NHP ORF and flanking regions.

5. DETAILED DESCRIPTION OF THE INVENTION

The NHP, described for the first time herein, are novel proteins that are widely expressed. NHP SEQ ID NO:1–5 are expressed in, inter alia, human cell lines, and human pituitary, lymph node, kidney, testis, thyroid, fetal kidney, and gene trapped cells. NHP SEQ ID NO:1–5 were compiled from gene trapped sequences in conjunction with sequences available in GENBANK, and cDNAs from a kidney mRNA (Edge Biosystems, Gaithersburg, Md.).

The NHPs, described for the first time in NHP SEQ ID NO:6–11 are novel proteins expressed in, inter alia, human cell lines, and human pituitary, lymph node, kidney, colon, and prostate cells. NHP SEQ ID NO:6–11 were compiled from sequences available in GENBANK, and cDNAs generated from kidney, prostate, and colon mRNA (Edge Biosystems, Gaithersburg, Md.).

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal (or hydrophobic transmembrane) sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–11 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–11, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–11 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–11.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–11 provides detailed information about transcriptional changes involved in a specific pathway, potentially leading to the identification of novel components or gene functions that manifest themselves as novel phenotypes.

Probes consisting of sequences first disclosed in SEQ ID NOS:1–11 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–11 can be utilized in microarrays or other assay formats, to screen collections of genetic material from patients who have a particular medical condition. These investigations can also be carried out using the sequences first disclosed in SEQ ID NOS:1–11 in silico and by comparing previously collected genetic databases and the disclosed sequences using computer software known to those in the art.

Thus the sequences first disclosed in SEQ ID NOS:1–11 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–11. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of, an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and corresponding deduced amino acid sequences of the described NHPs are presented in the Sequence Listing.

Expression analysis has provided evidence that the NHPs described in SEQ ID NO: 1–5 can be expressed in a relatively narrow range of human tissues. In addition to myosin III kinases, the NHPs described in SEQ ID NO: 1–5 also share significant similarity to a range of additional kinase families, including kinases associated with signal transduction, from a variety of phyla and species.

A number of polymorphisms can occur in the NHPs described in SEQ ID NO: 1–5, such as a possible A-G transition that can occur in the sequence region corresponding to, for example, nucleotide position 889 of SEQ ID NO:3 that can result in a K or E being present in the corresponding amino acid sequence represented by, for example, position 297 of SEQ ID NO:4. Similar myosin-like proteins, as well as uses and applications that are also applicable to the NHPs described in SEQ ID NO: 1–5, are described in U.S. Pat. No. 6,001,593 herein incorporated by reference in its entirety.

Expression analysis has provided evidence that the NHPs described in SEQ ID NO: 6–11 can be expressed in a relatively narrow range of human tissues. In addition to serine-threonine kinases, the NHPs described in SEQ ID NO: 6–11 also share significant similarity to a range of additional kinase families, again including kinases associated with signal transduction from a variety of phyla and species. The NHPs described in SEQ ID NO: 6–11 are apparently encoded on human chromosome 16.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPS AND NHP Polypeptides

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to a NHP, as reagents in assays for screening for compounds that can be used as pharmaceutical reagents useful in the therapeutic treatment of mental, biological, or medical disorders and diseases. Given the similarity information and expression data, the described NHPs can be targeted (by drugs, oligos, antibodies, etc.) in order to treat disease, or to therapeutically augment the efficacy of, for example, chemotherapeutic agents used in the treatment of breast or prostate cancer.

The Sequence Listing discloses the amino acid sequences encoded by the described NHP polynucleotides. The NHPs typically display have initiator methionines in DNA sequence contexts consistent with a translation initiation site.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian iruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^2$-nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes:A Practical Approach", New,RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ. This goal may be achieved by coupling of the NHP to a cytokine or other ligand that provides targeting specificity, and/or to a protein transducing domain (see generally U.S. applications Ser. No. 60/111,701 and 60/056,713, both of which are herein incorporated by reference, for examples of such transducing sequences) to facilitate passage across cellular membranes if needed and can optionally be engineered to include nuclear localization sequences when desired.

5.3 Antibodies To NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. A recombinant expression vector comprising the nucleic acid sequence of SEQ ID NO: 6.

2. A host cell comprising the vector of claim 1.

* * * * *

SEQUENCE LISTING

```
<160> NUMBER OF SEQ ID NOS: 11

<210> SEQ ID NO 1
<211> LENGTH: 717
<212> TYPE: DNA
```

```
<213> ORGANISM: homo sapiens

<400> SEQUENCE: 1

atgatgcttg gacttgaatc acttccagat cccacagaca cctgggaaat tatagagacc      60

attggtaaag gcacctatgg caaagtctac aaggtaacta acaagagaga tgggagcctg     120

gctgcagtga aaattctgga tccagtcagt gatatggatg aagaaattga ggcagaatac     180

aacattttgc agttccttcc taatcatccc aatgttgtaa agttttatgg gatgttttac     240

aaagcggatc actgtgtagg gggacagctg tggctggtcc tggagctgtg taatgggggc     300

tcagtcacyg agcttgtcaa aggtctactc agatgtggcc agcggttgga tgaagcaatg     360

atctcataca tcttgtacgg ggccctcttg ggccttcagc atttgcacaa caaccgaatc     420

atccaccgtg atgtgaaggg gaataacatt cttctgacaa cagaaggagg agttaagctc     480

gttgactttg gtgtttcagc tcaactcacc agtacacgtc tgcggagaaa cacatctgtt     540

ggcaccccat tctggatggc ccctgaggtc attgcctgtg agcagcagta tgactcttcc     600

tatgacgctc gctgtgacgt ctggtccttg ggatcacag ctattgaact gggggatgga      660

gaccctcccc tctttgacat gcatcctgtg aaaacactct ttaagattcc aaggtaa        717


<210> SEQ ID NO 2
<211> LENGTH: 238
<212> TYPE: PRT
<213> ORGANISM: homo sapiens

<400> SEQUENCE: 2

Met Met Leu Gly Leu Glu Ser Leu Pro Asp Pro Thr Asp Thr Trp Glu
 1               5                   10                  15

Ile Ile Glu Thr Ile Gly Lys Gly Thr Tyr Gly Lys Val Tyr Lys Val
            20                  25                  30

Thr Asn Lys Arg Asp Gly Ser Leu Ala Ala Val Lys Ile Leu Asp Pro
        35                  40                  45

Val Ser Asp Met Asp Glu Glu Ile Glu Ala Glu Tyr Asn Ile Leu Gln
    50                  55                  60

Phe Leu Pro Asn His Pro Asn Val Val Lys Phe Tyr Gly Met Phe Tyr
65                  70                  75                  80

Lys Ala Asp His Cys Val Gly Gly Gln Leu Trp Leu Val Leu Glu Leu
                85                  90                  95

Cys Asn Gly Gly Ser Val Thr Glu Leu Val Lys Gly Leu Leu Arg Cys
            100                 105                 110

Gly Gln Arg Leu Asp Glu Ala Met Ile Ser Tyr Ile Leu Tyr Gly Ala
        115                 120                 125

Leu Leu Gly Leu Gln His Leu His Asn Asn Arg Ile Ile His Arg Asp
    130                 135                 140

Val Lys Gly Asn Asn Ile Leu Leu Thr Thr Glu Gly Gly Val Lys Leu
145                 150                 155                 160

Val Asp Phe Gly Val Ser Ala Gln Leu Thr Ser Thr Arg Leu Arg Arg
                165                 170                 175

Asn Thr Ser Val Gly Thr Pro Phe Trp Met Ala Pro Glu Val Ile Ala
            180                 185                 190

Cys Glu Gln Gln Tyr Asp Ser Ser Tyr Asp Ala Arg Cys Asp Val Trp
        195                 200                 205

Ser Leu Gly Ile Thr Ala Ile Glu Leu Gly Asp Gly Asp Pro Pro Leu
    210                 215                 220

Phe Asp Met His Pro Val Lys Thr Leu Phe Lys Ile Pro Arg
```

-continued 225 230 235

<210> SEQ ID NO 3
<211> LENGTH: 3711
<212> TYPE: DNA
<213> ORGANISM: homo sapiens

<400> SEQUENCE: 3

```
atgatgcttg gacttgaatc acttccagat cccacagaca cctgggaaat tatagagacc     60
attggtaaag gcacctatgg caaagtctac aaggtaacta acaagagaga tgggagcctg    120
gctgcagtga aaattctgga tccagtcagt gatatggatg aagaaattga ggcagaatac    180
aacattttgc agttccttcc taatcatccc aatgttgtaa agttttatgg gatgttttac    240
aaagcggatc actgtgtagg gggacagctg tggctggtcc tggagctgtg taatgggggc    300
tcagtcacyg agcttgtcaa aggtctactc agatgtggcc agcggttgga tgaagcaatg    360
atctcataca tcttgtacgg ggccctcttg ggccttcagc atttgcacaa caaccgaatc    420
atccaccgtg atgtgaaggg gaataacatt cttctgacaa cagaaggagg agttaagctc    480
gttgactttg gtgtttcagc tcaactcacc agtacacgtc tgcggagaaa cacatctgtt    540
ggcaccccat tctggatggc ccctgaggtc attgcctgtg agcagcagta tgactcttcc    600
tatgacgctc gctgtgacgt ctggtccttg ggggatcacag ctattgaact gggggatgga    660
gaccctcccc tctttgacat gcatcctgtg aaaacactct ttaagattcc aagaaatcct    720
ccacctactt tacttcatcc agaaaaatgg tgtgaagaat tcaaccactt tatttcacag    780
tgtcttatta aggattttga aaggcgacct tccgtcacac atctccttga ccacccattt    840
attaaaggag tacatggaaa agttctgttt ctgcaaaaac agctggccra ggttctccaa    900
gaccagaagc atcaaaatcc tgttgctaaa accaggcatg agaggatgca taccagaaga    960
ccttatcatg tggaagatgc tgaaaaatac tgccttgagg atgatttggt caacctagag   1020
gttctggatg aggatacaat tatccatcag ttgcagaaac gttatgcaga cttgctaatt   1080
tacacatatg ttggagacat cttaattgcc ttaaacccct tccagaatct aagcatatac   1140
tctccacagt tttccagact ttatcatggg gtgaaacgcg cctccaaycc cccccacata   1200
tttgcatcag cagatgctgc ttaccagtgc atggttactc tcagcaaaga ccagtgcatt   1260
gtcatcagcg gagagagtgg ctctgggaag acagaaagcg cccacctgat tgttcarcat   1320
ttgactttct tgggaaaggc caataatcag accttgagag agaaaattct acaagtcaac   1380
tccctggtgg aagcctttgg gaactcatgc actgccatca atgacaactc gagccgtttt   1440
ggaaaatatc tggaaatgat gtttacacca actggagttg tgatgggggc aagaatctct   1500
gaatatctcc tggaaaaatc cagagttata aaacaggcag cgagagagaa aaattttcat   1560
atattttact atatttatgc tggtcttcat caccaaaaga agctttctga tttcagactt   1620
cctgaggaaa aacctcctag gtacatagct gatgaaactg gaagggtgat gcacgacata   1680
acttccaagg agtcttacag aagacaattc gaagcaattc agcattgctt caggattata   1740
gggttcacgg acaaagaggt gcactcagtg tacagaattt tggctgggat tttgaatatt   1800
gggaacattg agttcgcagc tatttcctct caacatcaga ctgataaaag tgaggtgccc   1860
aatgctgaag ctttgcaaaa tgctgcctct gttctgtgca ttagccctga agagctccag   1920
gaggccctca cctcccactg tgtggtcacc cggggcgaga ccatcatccg tgccaacact   1980
gtagacaggg ctgcggacgt tcgagacgcc atgtccaaag ccctgtatgg gaggctcttc   2040
agctggattg tgaatcgcat taatacactc ctgcagccag acgaaaacat atgtagtgca   2100
```

```
ggaggtggaa tgaatgtggg gatcttggat atctttggat tcgagaattt tcagagaaat   2160

tcatttgagc agctctgcat aaacatcgcc aatgagcaaa tccagtacta tttcaatcag   2220

catgtttttg ctcttgagca gatggaatat cagaatgaag gcattgatgc tatacccgtg   2280

gaatatgagg acaaccgccc gctcctggac atgttcctcc agaaacccct gggactgctt   2340

gcacttttgg atgaggaaag tcggtttccc caagcaactg accagaccct ggttgataaa   2400

tttgaagata atctacgatg caaatacttc tggaggccca aggagtggga actgtgcttt   2460

ggcattcagc attatgctgg aaaggtatta tatgatgctt ctggggttct tgagaaaaat   2520

agagacactc tccctgccga tgtggttgtg gtcctgagaa cgtcagaaaa caagcttctt   2580

cagcagctct tctcaatccc tctgaccaaa acaggtaatt tggcccagac aagagctagg   2640

ataacagtgg cctcaagttc tttgcctcca catttcagtg ctgggaaagc caaggtggac   2700

actctggagg tgatacggca tccggaagaa accaccaaca tgaagaggca aactgtggct   2760

tcttacttcc ggtattctct gatggacctg ctctccaaaa tggtggttgg acagccccac   2820

tttgtgcgct gcattaaacc caatgatgac cgagaggccc tgcagttctc tcgagagagg   2880

gtgctggccc agctccgctc cacagggatt ctggagacag tcagcatccg ccgccagggc   2940

tattcccacc gcatcctttt tgaagaattt gtgaaaaggt attattactt ggcattcaca   3000

gcacatcaaa cacctcttgc tagcaaagag agctgtgtgg ctatcttgga aaagtccaga   3060

ttagatcact gggtgctggg aaaaacaaag gtttttctca aatattacca tgttgagcaa   3120

ytaaatttgc tgcttcgaga agtcataggc agagtggttg tgctgcaggc atataccaag   3180

gggtggcttg gagccaggag atacaaaaag gtcagagaga agagagagaa gggagccatt   3240

gccatccagt cagcctggag aggatatgat gctcggagga aatttaagaa aataagcaac   3300

agaaggaatg agtctgctgc tcataatcaa gcaggggcca cttcaaacca aagcagtggg   3360

ccacattccc ccgtcgcagc aggtacgagg ggaagtgccg aggttcaaga ctgcagcgag   3420

cctggtgacc ataaagttct caggggctct gtacatcgta ggagccattc acaagcagaa   3480

tccaacaatg gccgtacaca gacttcaagc aactctcctg ctgtcacaga gaaaaatggg   3540

cattcacaag cccagagttc tccaaaaggg tgcgatatct tcgcaggaca tgcaaacaag   3600

gtagctggat atcttgattc caaagtaaat gtgtatcact ccttcagact catccaagtt   3660

cataggcatg aagcttgtct gcggctgcgt ggttggacca tccaaacttg a            3711
```

```
<210> SEQ ID NO 4
<211> LENGTH: 1236
<212> TYPE: PRT
<213> ORGANISM: homo sapiens

<400> SEQUENCE: 4

Met Met Leu Gly Leu Glu Ser Leu Pro Asp Pro Thr Asp Thr Trp Glu
 1               5                  10                  15

Ile Ile Glu Thr Ile Gly Lys Gly Thr Tyr Gly Lys Val Tyr Lys Val
            20                  25                  30

Thr Asn Lys Arg Asp Gly Ser Leu Ala Ala Val Lys Ile Leu Asp Pro
        35                  40                  45

Val Ser Asp Met Asp Glu Glu Ile Glu Ala Glu Tyr Asn Ile Leu Gln
    50                  55                  60

Phe Leu Pro Asn His Pro Asn Val Val Lys Phe Tyr Gly Met Phe Tyr
65                  70                  75                  80

Lys Ala Asp His Cys Val Gly Gly Gln Leu Trp Leu Val Leu Glu Leu
```

-continued

```
                85                  90                  95

Cys Asn Gly Gly Ser Val Thr Glu Leu Val Lys Gly Leu Leu Arg Cys
            100                 105                 110

Gly Gln Arg Leu Asp Glu Ala Met Ile Ser Tyr Ile Leu Tyr Gly Ala
        115                 120                 125

Leu Leu Gly Leu Gln His Leu His Asn Asn Arg Ile Ile His Arg Asp
    130                 135                 140

Val Lys Gly Asn Asn Ile Leu Leu Thr Thr Glu Gly Gly Val Lys Leu
145                 150                 155                 160

Val Asp Phe Gly Val Ser Ala Gln Leu Thr Ser Thr Arg Leu Arg Arg
                165                 170                 175

Asn Thr Ser Val Gly Thr Pro Phe Trp Met Ala Pro Glu Val Ile Ala
            180                 185                 190

Cys Glu Gln Gln Tyr Asp Ser Ser Tyr Asp Ala Arg Cys Asp Val Trp
        195                 200                 205

Ser Leu Gly Ile Thr Ala Ile Glu Leu Gly Asp Gly Asp Pro Pro Leu
    210                 215                 220

Phe Asp Met His Pro Val Lys Thr Leu Phe Lys Ile Pro Arg Asn Pro
225                 230                 235                 240

Pro Pro Thr Leu Leu His Pro Glu Lys Trp Cys Glu Glu Phe Asn His
                245                 250                 255

Phe Ile Ser Gln Cys Leu Ile Lys Asp Phe Glu Arg Arg Pro Ser Val
            260                 265                 270

Thr His Leu Leu Asp His Pro Phe Ile Lys Gly Val His Gly Lys Val
        275                 280                 285

Leu Phe Leu Gln Lys Gln Leu Ala Lys Val Leu Gln Asp Gln Lys His
    290                 295                 300

Gln Asn Pro Val Ala Lys Thr Arg His Glu Arg Met His Thr Arg Arg
305                 310                 315                 320

Pro Tyr His Val Glu Asp Ala Glu Lys Tyr Cys Leu Glu Asp Asp Leu
                325                 330                 335

Val Asn Leu Glu Val Leu Asp Glu Asp Thr Ile Ile His Gln Leu Gln
            340                 345                 350

Lys Arg Tyr Ala Asp Leu Leu Ile Tyr Thr Tyr Val Gly Asp Ile Leu
        355                 360                 365

Ile Ala Leu Asn Pro Phe Gln Asn Leu Ser Ile Tyr Ser Pro Gln Phe
    370                 375                 380

Ser Arg Leu Tyr His Gly Val Lys Arg Ala Ser Asn Pro Pro His Ile
385                 390                 395                 400

Phe Ala Ser Ala Asp Ala Ala Tyr Gln Cys Met Val Thr Leu Ser Lys
                405                 410                 415

Asp Gln Cys Ile Val Ile Ser Gly Glu Ser Gly Ser Gly Lys Thr Glu
            420                 425                 430

Ser Ala His Leu Ile Val Gln His Leu Thr Phe Leu Gly Lys Ala Asn
        435                 440                 445

Asn Gln Thr Leu Arg Glu Lys Ile Leu Gln Val Asn Ser Leu Val Glu
    450                 455                 460

Ala Phe Gly Asn Ser Cys Thr Ala Ile Asn Asp Asn Ser Ser Arg Phe
465                 470                 475                 480

Gly Lys Tyr Leu Glu Met Met Phe Thr Pro Thr Gly Val Val Met Gly
                485                 490                 495

Ala Arg Ile Ser Glu Tyr Leu Leu Glu Lys Ser Arg Val Ile Lys Gln
            500                 505                 510
```

```
Ala Ala Arg Glu Lys Asn Phe His Ile Phe Tyr Tyr Ile Tyr Ala Gly
        515                 520                 525

Leu His His Gln Lys Lys Leu Ser Asp Phe Arg Leu Pro Glu Glu Lys
    530                 535                 540

Pro Pro Arg Tyr Ile Ala Asp Glu Thr Gly Arg Val Met His Asp Ile
545                 550                 555                 560

Thr Ser Lys Glu Ser Tyr Arg Arg Gln Phe Glu Ala Ile Gln His Cys
                565                 570                 575

Phe Arg Ile Ile Gly Phe Thr Asp Lys Glu Val His Ser Val Tyr Arg
            580                 585                 590

Ile Leu Ala Gly Ile Leu Asn Ile Gly Asn Ile Glu Phe Ala Ala Ile
        595                 600                 605

Ser Ser Gln His Gln Thr Asp Lys Ser Glu Val Pro Asn Ala Glu Ala
    610                 615                 620

Leu Gln Asn Ala Ala Ser Val Leu Cys Ile Ser Pro Glu Glu Leu Gln
625                 630                 635                 640

Glu Ala Leu Thr Ser His Cys Val Val Thr Arg Gly Glu Thr Ile Ile
                645                 650                 655

Arg Ala Asn Thr Val Asp Arg Ala Ala Asp Val Arg Asp Ala Met Ser
            660                 665                 670

Lys Ala Leu Tyr Gly Arg Leu Phe Ser Trp Ile Val Asn Arg Ile Asn
        675                 680                 685

Thr Leu Leu Gln Pro Asp Glu Asn Ile Cys Ser Ala Gly Gly Gly Met
    690                 695                 700

Asn Val Gly Ile Leu Asp Ile Phe Gly Phe Glu Asn Phe Gln Arg Asn
705                 710                 715                 720

Ser Phe Glu Gln Leu Cys Ile Asn Ile Ala Asn Glu Gln Ile Gln Tyr
                725                 730                 735

Tyr Phe Asn Gln His Val Phe Ala Leu Glu Gln Met Glu Tyr Gln Asn
            740                 745                 750

Glu Gly Ile Asp Ala Ile Pro Val Glu Tyr Glu Asp Asn Arg Pro Leu
        755                 760                 765

Leu Asp Met Phe Leu Gln Lys Pro Leu Gly Leu Leu Ala Leu Leu Asp
    770                 775                 780

Glu Glu Ser Arg Phe Pro Gln Ala Thr Asp Gln Thr Leu Val Asp Lys
785                 790                 795                 800

Phe Glu Asp Asn Leu Arg Cys Lys Tyr Phe Trp Arg Pro Lys Gly Val
                805                 810                 815

Glu Leu Cys Phe Gly Ile Gln His Tyr Ala Gly Lys Val Leu Tyr Asp
            820                 825                 830

Ala Ser Gly Val Leu Glu Lys Asn Arg Asp Thr Leu Pro Ala Asp Val
        835                 840                 845

Val Val Val Leu Arg Thr Ser Glu Asn Lys Leu Leu Gln Gln Leu Phe
    850                 855                 860

Ser Ile Pro Leu Thr Lys Thr Gly Asn Leu Ala Gln Thr Arg Ala Arg
865                 870                 875                 880

Ile Thr Val Ala Ser Ser Ser Leu Pro Pro His Phe Ser Ala Gly Lys
                885                 890                 895

Ala Lys Val Asp Thr Leu Glu Val Ile Arg His Pro Glu Glu Thr Thr
            900                 905                 910

Asn Met Lys Arg Gln Thr Val Ala Ser Tyr Phe Arg Tyr Ser Leu Met
        915                 920                 925
```

-continued

```
Asp Leu Leu Ser Lys Met Val Val Gly Gln Pro His Phe Val Arg Cys
    930                 935                 940

Ile Lys Pro Asn Asp Asp Arg Glu Ala Leu Gln Phe Ser Arg Glu Arg
945                 950                 955                 960

Val Leu Ala Gln Leu Arg Ser Thr Gly Ile Leu Glu Thr Val Ser Ile
                965                 970                 975

Arg Arg Gln Gly Tyr Ser His Arg Ile Leu Phe Glu Glu Phe Val Lys
            980                 985                 990

Arg Tyr Tyr Tyr Leu Ala Phe Thr Ala His Gln Thr Pro Leu Ala Ser
        995                 1000                1005

Lys Glu Ser Cys Val Ala Ile Leu Glu Lys Ser Arg Leu Asp His Trp
    1010                1015                1020

Val Leu Gly Lys Thr Lys Val Phe Leu Lys Tyr Tyr His Val Glu Gln
1025                1030                1035                1040

Leu Asn Leu Leu Leu Arg Glu Val Ile Gly Arg Val Val Val Leu Gln
                1045                1050                1055

Ala Tyr Thr Lys Gly Trp Leu Gly Ala Arg Arg Tyr Lys Lys Val Arg
            1060                1065                1070

Glu Lys Arg Glu Lys Gly Ala Ile Ala Ile Gln Ser Ala Trp Arg Gly
        1075                1080                1085

Tyr Asp Ala Arg Arg Lys Phe Lys Lys Ile Ser Asn Arg Arg Asn Glu
    1090                1095                1100

Ser Ala Ala His Asn Gln Ala Gly Ala Thr Ser Asn Gln Ser Ser Gly
1105                1110                1115                1120

Pro His Ser Pro Val Ala Ala Gly Thr Arg Gly Ser Ala Glu Val Gln
                1125                1130                1135

Asp Cys Ser Glu Pro Gly Asp His Lys Val Leu Arg Gly Ser Val His
            1140                1145                1150

Arg Arg Ser His Ser Gln Ala Glu Ser Asn Asn Gly Arg Thr Gln Thr
        1155                1160                1165

Ser Ser Asn Ser Pro Ala Val Thr Glu Lys Asn Gly His Ser Gln Ala
    1170                1175                1180

Gln Ser Ser Pro Lys Gly Cys Asp Ile Phe Ala Gly His Ala Asn Lys
1185                1190                1195                1200

Val Ala Gly Tyr Leu Asp Ser Lys Val Asn Val Tyr His Ser Phe Arg
                1205                1210                1215

Leu Ile Gln Val His Arg His Glu Ala Cys Leu Arg Leu Arg Gly Trp
            1220                1225                1230

Thr Ile Gln Thr
        1235
```

<210> SEQ ID NO 5
<211> LENGTH: 4034
<212> TYPE: DNA
<213> ORGANISM: homo sapiens
<220> FEATURE:
<221> NAME/KEY: misc_feature
<222> LOCATION: (1)...(4034)
<223> OTHER INFORMATION: n = A,T,C or G

<400> SEQUENCE: 5

```
ttttcaacaa gatggagtct tgctctgttt cccagcctgt agtgcagtga cacagtcttg     60

gctcactgta acctctgcct cctgggttca agtgattctc ctgcctcagc ctcctgagta    120

gctgggatta caggaaacat ctgtatggat tatttcacta taatcctatg atgcttggac    180

ttgaatcact tccagatccc acagacacct gggaaattat agagaccatt ggtaaaggca    240
```

-continued

```
cctatggcaa agtctacaag gtaactaaca agagagatgg gagcctggct gcagtgaaaa    300
ttctggatcc agtcagtgat atggatgaag aaattgaggc agaatacaac attttgcagt    360
tccttcctaa tcatcccaat gttgtaaagt tttatgggat gttttacaaa gcggatcact    420
gtgtaggggg acagctgtgg ctggtcctgg agctgtgtaa tgggggctca gtcacygagc    480
ttgtcaaagg tctactcaga tgtggccagc ggttggatga agcaatgatc tcatacatct    540
tgtacggggc cctcttgggc cttcagcatt tgcacaacaa ccgaatcatc caccgtgatg    600
tgaaggggaa taacattctt ctgacaacag aaggaggagt taagctcgtt gactttggtg    660
tttcagctca actcaccagt acacgtctgc ggagaaacac atctgttggc accccattct    720
ggatggcccc tgaggtcatt gcctgtgagc agcagtatga ctcttcctat gacgctcgct    780
gtgacgtctg gtccttgggg atcacagcta ttgaactggg ggatggagac cctcccctct    840
ttgacatgca tcctgtgaaa acactcttta agattccaag aaatcctcca cctactttac    900
ttcatccaga aaaatggtgt gaagaattca accactttat ttcacagtgt cttattaagg    960
attttgaaag gcgaccttcc gtcacacatc tccttgacca cccatttatt aaaggagtac   1020
atggaaaagt tctgtttctg caaaaacagc tggccragg t tctccaagac cagaagcatc   1080
aaaatcctgt tgctaaaacc aggcatgaga ggatgcatac cagaagacct tatcatgtgg   1140
aagatgctga aaaatactgc cttgaggatg atttggtcaa cctagaggtt ctggatgagg   1200
atacaattat ccatcagttg cagaaacgtt atgcagactt gctaatttac acatatgttg   1260
gagacatctt aattgcctta aaccccttcc agaatctaag catatactct ccacagtttt   1320
ccagacttta tcatggggtg aaacgcgcct ccaaycccc ccacatattt gcatcagcag   1380
atgctgctta ccagtgcatg gttactctca gcaaagacca gtgcattgtc atcagcggag   1440
agagtggctc tgggaagaca gaaagcgccc acctgattgt tcarcatttg actttcttgg   1500
gaaaggccaa taatcagacc ttgagagaga aaattctaca agtcaactcc ctggtggaag   1560
cctttgggaa ctcatgcact gccatcaatg acaactcgag ccgttttgga aaatatctgg   1620
aaatgatgtt tacaccaact ggagttgtga tgggggcaag aatctctgaa tatctcctgg   1680
aaaaatccag agttataaaa caggcagcga gagagaaaaa ttttcatata ttttactata   1740
tttatgctgg tcttcatcac caaaagaagc tttctgattt cagacttcct gaggaaaaac   1800
ctcctaggta catagctgat gaaactggaa gggtgatgca cgacataact tccaaggagt   1860
cttacagaag acaattcgaa gcaattcagc attgcttcag gattataggg ttcacggaca   1920
aagaggtgca ctcagtgtac agaattttgg ctgggatttt gaatattggg aacattgagt   1980
tcgcagctat ttcctctcaa catcagactg ataaaagtga ggtgcccaat gctgaagctt   2040
tgcaaaatgc tgcctctgtt ctgtgcatta gccctgaaga gctccaggag gccctcacct   2100
cccactgtgt ggtcacccgg ggcgagacca tcatccgtgc caacactgta gacagggctg   2160
cggacgttcg agacgccatg tccaaagccc tgtatgggag gctcttcagc tggattgtga   2220
atcgcattaa tacactcctg cagccagacg aaaacatatg tagtgcagga ggtggaatga   2280
atgtggggat cttggatatc tttggattcg agaattttca gagaaattca tttgagcagc   2340
tctgcataaa catcgccaat gagcaaatcc agtactattt caatcagcat gtttttgctc   2400
ttgagcagat ggaatatcag aatgaaggca ttgatgctat acccgtggaa tatgaggaca   2460
accgcccgct cctggacatg ttcctccaga aacccctggg actgcttgca cttttggatg   2520
aggaaagtcg gtttccccaa gcaactgacc agaccctggt tgataaattt gaagataatc   2580
```

-continued

```
tacgatgcaa atacttctgg aggcccaaag gagtggaact gtgctttggc attcagcatt   2640

atgctggaaa ggtattatat gatgcttctg gggttcttga gaaaaataga gacactctcc   2700

ctgccgatgt ggttgtggtc ctgagaacgt cagaaaacaa gcttcttcag cagctcttct   2760

caatccctct gaccaaaaca ggtaatttgg cccagacaag agctaggata acagtggcct   2820

caagttcttt gcctccacat ttcagtgctg ggaaagccaa ggtggacact ctggaggtga   2880

tacggcatcc ggaagaaacc accaacatga agaggcaaac tgtggcttct tacttccggt   2940

attctctgat ggacctgctc tccaaaatgg tggttggaca gccccacttt gtgcgctgca   3000

ttaaacccaa tgatgaccga gaggccctgc agttctctcg agagagggtg ctggcccagc   3060

tccgctccac agggattctg gagacagtca gcatccgccg ccagggctat tcccaccgca   3120

tcctttttga agaatttgtg aaaaggtatt attacttggc attcacagca catcaaacac   3180

ctcttgctag caaagagagc tgtgtggcta tcttggaaaa gtccagatta gatcactggg   3240

tgctgggaaa aacaaaggtt tttctcaaat attaccatgt tgagcaayta aatttgctgc   3300

ttcgagaagt cataggcaga gtggttgtgc tgcaggcata taccaagggg tggcttggag   3360

ccaggagata caaaaaggtc agagagaaga gagagaaggg agccattgcc atccagtcag   3420

cctggagagg atatgatgct cggaggaaat ttaagaaaat aagcaacaga aggaatgagt   3480

ctgctgctca taatcaagca ggggccactt caaaccaaag cagtgggcca cattccccccg   3540

tcgcagcagg tacgaggga agtgccgagg ttcaagactg cagcgagcct ggtgaccata   3600

aagttctcag ggctctgta catcgtagga gccattcaca agcagaatcc aacaatggcc   3660

gtacacagac ttcaagcaac tctcctgctg tcacagagaa aaatgggcat tcacaagccc   3720

agagttctcc aaaagggtgc gatatcttcg caggacatgc aaacaaggta gctggatatc   3780

ttgattccaa agtaaatgtg tatcactcct tcagactcat ccaagttcat aggcatgaag   3840

cttgtctgcg gctgcgtggt tggaccatcc aaacttgaaa ctgttagtga tattttgaag   3900

tctttgagac aaaagcccag cttgctgaag aactttggtt cagtagagag acagggaggt   3960

acaggggaga gagaatcaaa agcctggaaa tttgctgctg agaataaatg ttagctgctc   4020

cctggnngna aaaa                                                     4034
```

<210> SEQ ID NO 6
<211> LENGTH: 2925
<212> TYPE: DNA
<213> ORGANISM: homo sapiens

<400> SEQUENCE: 6

```
atgagaaggg cggggatcgg cgaggactcc aggctggggt tgcaggccca gccaggggcg     60

gagccttctc cgggtcgggc ggggacagag cgctcccttg gaggcaccca gggacctggc    120

cagccgtgca gctgcccagg cgctatggcg agtgcggtca gggggtcgag gccgtggccc    180

cggctggggc tccagctcca gttcgcggcg ctgctgctcg ggacgctgag tccacaggtt    240

catactctca ggccagagaa cctcctgctg gtgtccacct tggatggaag tctccacgca    300

ctaagcaagc agacagggga cctgaagtgg actctgaggg atgatcccgt catcgaagga    360

ccaatgtacg tcacagaaat ggcctttctc tctgacccag cagatggcag cctgtacatc    420

ttggggaccc aaaaacaaca gggattaatg aaactgccat tcaccatccc tgagctggtt    480

catgcctctc cctgccgcag ctctgatggg gtcttctaca caggccggaa gcaggatgcc    540

tggtttgtgg tggaccctga gtcaggggag acccagatga cactgaccac agagggtccc    600

tccacccccc gcctctacat tggccgaaca cagtatacgg tcaccatgca tgacccaaga    660
```

-continued

```
gccccagccc tgcgctggaa caccacctac cgccgctact cagcgccccc catggatggc    720
tcacctggga aatacatgag ccacctggcg tcctgcggga tgggcctgct gctcactgtg    780
gacccaggaa gcgggacggt gctgtggaca caggacctgg gcgtgcctgt gatgggcgtc    840
tacacctggc accaggacgg cctgcgccag ctgccgcatc tcacgctggc tcgagacact    900
ctgcatttcc tcgccctccg ctggggccac atccgactgc ctgcctcagg cccccgggac    960
acagccaccc tcttctctac cttggacacc cagctgctaa tgacgctgta tgtggggaag   1020
gatgaaactg gcttctatgt ctytaaagca ctggtccaca caggagtggc cctggtgcct   1080
cgtggactga ccctggcccc cgcagatggc cccaccacag atgaggtgac actccaagtc   1140
tcaggagagc gagagggctc acccagcact gctgttagat acccctcagg cagtgtggcc   1200
ctcccaagcc agtggctgct cattggacac cacgagctac ccccagtcct gcacaccacc   1260
atgctgaggg tccatcccac cctggggagt ggaactgcag agacaagacc tccagagaat   1320
acccaggccc cagccttctt cttggagcta ttgagcctga gccgagagaa actttgggac   1380
tccgagctgc atccagaaga aaaaactcca gactcttact tggggctggg accccaagac   1440
ctgctggcag ctagcctcac tgctgtcctc ctgggagggt ggattctctt tgtgatgagg   1500
cagcaacagc cgcaggtggt ggagaagcag caggagaccc ccctggcacc tgcagacttt   1560
gctcacatct cccaggatgc ccagtccctg cactcggggg ccagccggag gagccagaag   1620
aggcttcaga gtccctcaaa gcaagcccag ccactcgacg accctgaagc tgagcaactc   1680
accgtagtgg ggaagatttc cttcaatccc aaggacgtgc tgggccgcgg ggcaggcggg   1740
actttcgttt tccggggaca gtttgaggga cgggcagtgg ctgtcaagcg gctcctccgc   1800
gagtgctttg gcctggttcg gcgggaagtt caactgctgc aggagtctga caggcacccc   1860
aacgtgctcc gctacttctg caccgagcgg ggaccccagt tccactacat tgccctggag   1920
ctctgccggg cctccttgca ggagtacgta gaaaacccgg acctggatcg cgggggtctg   1980
gagcccgagg tcgtgctgca gcagctgatg tctggcctgg cccacctgca ctctttacac   2040
atagtgcacc gggacctgaa gccaggaaat attctcatca ccgggcctga cagccagggc   2100
ctgggcagag tggtgctctc agacttcggc ctctgcaaga agctgcctgc tggccgctgt   2160
agcttcagcc tccactccgg catccccggc acggaaggct ggatggcgcc cgagcttctg   2220
cagctcctgc caccagacag tcctaccagc gctgtggaca tcttctctgc aggctgcgtg   2280
ttctactacg tgctttctgg tggcagccac ccctttggag acagtcttta tcgccaggca   2340
aacatcctca caggggctcc ctgtctggct cacctggagg aagaggtcca cgacaaggtg   2400
gttgcccggg acctggttgg agccatgttg agcccactgc cgcagccacg cccctctgcc   2460
ccccaggtgc tggcccaccc cttcttttgg agcagagcca agcaactcca gttcttccag   2520
gacgtcagtg actggctgga gaaggagtcc gagcaggagc ccctggtgag ggcactggag   2580
gcgggaggct gcgcagtggt ccgggacaac tggcacgagc acatctccat gccgctgcag   2640
acagatctga gaaagttccg gtcctataag gggacatcag tgcgagacct gctccgtgct   2700
gtgaggaaca agaagcacca ctacagggag ctcccagttg aggtgcgaca ggcactcggc   2760
caagtccctg atggcttcgt ccagtacttc acaaaccgct tcccacggct gctcctccac   2820
acgcaccgag ccatgaggag ctgcgcctct gagagcctct tcctgcccta ctacccgcca   2880
gactcagagg ccaggaggcc atgccctggg gccacaggga ggtga                     2925
```

<210> SEQ ID NO 7

-continued

```
<211> LENGTH: 974
<212> TYPE: PRT
<213> ORGANISM: homo sapiens
<220> FEATURE:
<221> NAME/KEY: VARIANT
<222> LOCATION: (1)...(974)
<223> OTHER INFORMATION: Xaa = Any Amino Acid

<400> SEQUENCE: 7

Met Arg Arg Ala Gly Ile Gly Glu Asp Ser Arg Leu Gly Leu Gln Ala
 1               5                  10                  15

Gln Pro Gly Ala Glu Pro Ser Pro Gly Arg Ala Gly Thr Glu Arg Ser
            20                  25                  30

Leu Gly Gly Thr Gln Gly Pro Gly Gln Pro Cys Ser Cys Pro Gly Ala
        35                  40                  45

Met Ala Ser Ala Val Arg Gly Ser Arg Pro Trp Pro Arg Leu Gly Leu
    50                  55                  60

Gln Leu Gln Phe Ala Ala Leu Leu Leu Gly Thr Leu Ser Pro Gln Val
65                  70                  75                  80

His Thr Leu Arg Pro Glu Asn Leu Leu Leu Val Ser Thr Leu Asp Gly
                85                  90                  95

Ser Leu His Ala Leu Ser Lys Gln Thr Gly Asp Leu Lys Trp Thr Leu
            100                 105                 110

Arg Asp Asp Pro Val Ile Glu Gly Pro Met Tyr Val Thr Glu Met Ala
        115                 120                 125

Phe Leu Ser Asp Pro Ala Asp Gly Ser Leu Tyr Ile Leu Gly Thr Gln
    130                 135                 140

Lys Gln Gln Gly Leu Met Lys Leu Pro Phe Thr Ile Pro Glu Leu Val
145                 150                 155                 160

His Ala Ser Pro Cys Arg Ser Ser Asp Gly Val Phe Tyr Thr Gly Arg
                165                 170                 175

Lys Gln Asp Ala Trp Phe Val Val Asp Pro Glu Ser Gly Glu Thr Gln
            180                 185                 190

Met Thr Leu Thr Thr Glu Gly Pro Ser Thr Pro Arg Leu Tyr Ile Gly
        195                 200                 205

Arg Thr Gln Tyr Thr Val Thr Met His Asp Pro Arg Ala Pro Ala Leu
    210                 215                 220

Arg Trp Asn Thr Thr Tyr Arg Arg Tyr Ser Ala Pro Pro Met Asp Gly
225                 230                 235                 240

Ser Pro Gly Lys Tyr Met Ser His Leu Ala Ser Cys Gly Met Gly Leu
                245                 250                 255

Leu Leu Thr Val Asp Pro Gly Ser Gly Thr Val Leu Trp Thr Gln Asp
            260                 265                 270

Leu Gly Val Pro Val Met Gly Val Tyr Thr Trp His Gln Asp Gly Leu
        275                 280                 285

Arg Gln Leu Pro His Leu Thr Leu Ala Arg Asp Thr Leu His Phe Leu
    290                 295                 300

Ala Leu Arg Trp Gly His Ile Arg Leu Pro Ala Ser Gly Pro Arg Asp
305                 310                 315                 320

Thr Ala Thr Leu Phe Ser Thr Leu Asp Thr Gln Leu Leu Met Thr Leu
                325                 330                 335

Tyr Val Gly Lys Asp Glu Thr Gly Phe Tyr Val Xaa Lys Ala Leu Val
            340                 345                 350

His Thr Gly Val Ala Leu Val Pro Arg Gly Leu Thr Leu Ala Pro Ala
        355                 360                 365
```

-continued

```
Asp Gly Pro Thr Thr Asp Glu Val Thr Leu Gln Val Ser Gly Glu Arg
    370                 375                 380

Glu Gly Ser Pro Ser Thr Ala Val Arg Tyr Pro Ser Gly Ser Val Ala
385                 390                 395                 400

Leu Pro Ser Gln Trp Leu Leu Ile Gly His His Glu Leu Pro Pro Val
                405                 410                 415

Leu His Thr Thr Met Leu Arg Val His Pro Thr Leu Gly Ser Gly Thr
            420                 425                 430

Ala Glu Thr Arg Pro Pro Glu Asn Thr Gln Ala Pro Ala Phe Phe Leu
        435                 440                 445

Glu Leu Leu Ser Leu Ser Arg Glu Lys Leu Trp Asp Ser Glu Leu His
    450                 455                 460

Pro Glu Glu Lys Thr Pro Asp Ser Tyr Leu Gly Leu Gly Pro Gln Asp
465                 470                 475                 480

Leu Leu Ala Ala Ser Leu Thr Ala Val Leu Leu Gly Gly Trp Ile Leu
                485                 490                 495

Phe Val Met Arg Gln Gln Gln Pro Gln Val Val Glu Lys Gln Gln Glu
            500                 505                 510

Thr Pro Leu Ala Pro Ala Asp Phe Ala His Ile Ser Gln Asp Ala Gln
        515                 520                 525

Ser Leu His Ser Gly Ala Ser Arg Arg Ser Gln Lys Arg Leu Gln Ser
    530                 535                 540

Pro Ser Lys Gln Ala Gln Pro Leu Asp Asp Pro Glu Ala Glu Gln Leu
545                 550                 555                 560

Thr Val Val Gly Lys Ile Ser Phe Asn Pro Lys Asp Val Leu Gly Arg
                565                 570                 575

Gly Ala Gly Gly Thr Phe Val Phe Arg Gly Gln Phe Glu Gly Arg Ala
            580                 585                 590

Val Ala Val Lys Arg Leu Leu Arg Glu Cys Phe Gly Leu Val Arg Arg
        595                 600                 605

Glu Val Gln Leu Leu Gln Glu Ser Asp Arg His Pro Asn Val Leu Arg
    610                 615                 620

Tyr Phe Cys Thr Glu Arg Gly Pro Gln Phe His Tyr Ile Ala Leu Glu
625                 630                 635                 640

Leu Cys Arg Ala Ser Leu Gln Glu Tyr Val Glu Asn Pro Asp Leu Asp
                645                 650                 655

Arg Gly Gly Leu Glu Pro Glu Val Val Leu Gln Gln Leu Met Ser Gly
            660                 665                 670

Leu Ala His Leu His Ser Leu His Ile Val His Arg Asp Leu Lys Pro
        675                 680                 685

Gly Asn Ile Leu Ile Thr Gly Pro Asp Ser Gln Gly Leu Gly Arg Val
    690                 695                 700

Val Leu Ser Asp Phe Gly Leu Cys Lys Lys Leu Pro Ala Gly Arg Cys
705                 710                 715                 720

Ser Phe Ser Leu His Ser Gly Ile Pro Gly Thr Glu Gly Trp Met Ala
                725                 730                 735

Pro Glu Leu Leu Gln Leu Leu Pro Pro Asp Ser Pro Thr Ser Ala Val
            740                 745                 750

Asp Ile Phe Ser Ala Gly Cys Val Phe Tyr Tyr Val Leu Ser Gly Gly
        755                 760                 765

Ser His Pro Phe Gly Asp Ser Leu Tyr Arg Gln Ala Asn Ile Leu Thr
    770                 775                 780

Gly Ala Pro Cys Leu Ala His Leu Glu Glu Glu Val His Asp Lys Val
```

-continued

```
785                 790                 795                 800

Val Ala Arg Asp Leu Val Gly Ala Met Leu Ser Pro Leu Pro Gln Pro
                805                 810                 815

Arg Pro Ser Ala Pro Gln Val Leu Ala His Pro Phe Phe Trp Ser Arg
            820                 825                 830

Ala Lys Gln Leu Gln Phe Phe Gln Asp Val Ser Asp Trp Leu Glu Lys
        835                 840                 845

Glu Ser Glu Gln Glu Pro Leu Val Arg Ala Leu Glu Ala Gly Gly Cys
    850                 855                 860

Ala Val Val Arg Asp Asn Trp His Glu His Ile Ser Met Pro Leu Gln
865                 870                 875                 880

Thr Asp Leu Arg Lys Phe Arg Ser Tyr Lys Gly Thr Ser Val Arg Asp
                885                 890                 895

Leu Leu Arg Ala Val Arg Asn Lys Lys His His Tyr Arg Glu Leu Pro
            900                 905                 910

Val Glu Val Arg Gln Ala Leu Gly Gln Val Pro Asp Gly Phe Val Gln
        915                 920                 925

Tyr Phe Thr Asn Arg Phe Pro Arg Leu Leu Leu His Thr His Arg Ala
    930                 935                 940

Met Arg Ser Cys Ala Ser Glu Ser Leu Phe Leu Pro Tyr Tyr Pro Pro
945                 950                 955                 960

Asp Ser Glu Ala Arg Arg Pro Cys Pro Gly Ala Thr Gly Arg
                965                 970
```

<210> SEQ ID NO 8
<211> LENGTH: 2769
<212> TYPE: DNA
<213> ORGANISM: homo sapiens

<400> SEQUENCE: 8

```
atgagaaggg cggggatcgg cgaggactcc aggctggggt tgcaggccca gccaggggcg      60

gagccttctc cgggtcgggc ggggacagag cgctcccttg gaggcaccca gggacctggc     120

cagccgtgca gctgcccagg cgctatggcg agtgcggtca gggggtcgag gccgtggccc     180

cggctggggc tccagctcca gttcgcggcg ctgctgctcg ggacgctgag tccacaggtt     240

catactctca ggccagagaa cctcctgctg gtgtccacct tggatggaag tctccacgca     300

ctaagcaagc agacagggga cctgaagtgg actctgaggg atgatcccgt catcgaagga     360

ccaatgtacg tcacagaaat ggcctttctc tctgacccag cagatggcag cctgtacatc     420

ttggggaccc aaaaacaaca gggattaatg aaactgccat tcaccatccc tgagctggtt     480

catgcctctc cctgccgcag ctctgatggg gtcttctaca caggccggaa gcaggatgcc     540

tggtttgtgg tggaccctga gtcaggggag acccagatga cactgaccac agagggtccc     600

tccacccccc gcctctacat tggccgaaca cagtatacgg tcaccatgca tgacccaaga     660

gccccagccc tgcgctggaa caccacctac cgccgctact cagcgccccc catggatggc     720

tcacctggga aatacatgag ccacctggcg tcctgcggga tgggcctgct gctcactgtg     780

gacccaggaa gcgggacggt gctgtggaca caggacctgg gcgtgcctgt gatgggcgtc     840

tacacctggc accaggacgg cctgcgccag ctgccgcatc tcacgctggc tcgagacact     900

ctgcatttcc tcgccctccg ctggggccac atccgactgc ctgcctcagg cccccgggac     960

acagccaccc tcttctctac cttggacacc cagctgctaa tgacgctgta tgtggggaag    1020

gatgaaactg gcttctatgt ctytaaagca ctggtccaca caggagtggc cctggtgcct    1080
```

-continued

```
cgtggactga ccctggcccc cgcagatggc cccaccacag atgaggtgac actccaagtc   1140

tcaggagagc gagagggctc acccagcact gctgttagat acccctcagg cagtgtggcc   1200

ctcccaagcc agtggctgct cattggacac cacgagctac cccagtcct gcacaccacc    1260

atgctgaggg tccatcccac cctggggagt ggaactgcag agacaagacc tccagagaat   1320

acccaggccc cagccttctt cttggagcaa cagccgcagg tggtggagaa gcagcaggag   1380

accccctgg cacctgcaga ctttgctcac atctcccagg atgcccagtc cctgcactcg    1440

ggggccagcc ggaggagcca gaagaggctt cagagtccct caaagcaagc ccagccactc   1500

gacgaccctg aagctgagca actcaccgta gtggggaaga tttccttcaa tcccaaggac   1560

gtgctgggcc gcggggcagg cgggactttc gttttccggg gacagtttga gggacgggca   1620

gtggctgtca agcggctcct ccgcgagtgc tttggcctgg ttcggcggga agttcaactg   1680

ctgcaggagt ctgacaggca ccccaacgtg ctccgctact tctgcaccga gcggggaccc   1740

cagttccact acattgccct ggagctctgc cgggcctcct tgcaggagta cgtagaaaac   1800

ccggacctgg atcgcggggg tctggagccc gaggtcgtgc tgcagcagct gatgtctggc   1860

ctggcccacc tgcactcttt acacatagtg caccgggacc tgaagccagg aaatattctc   1920

atcaccgggc ctgacagcca gggcctgggc agagtggtgc tctcagactt cggcctctgc   1980

aagaagctgc ctgctggccg ctgtagcttc agcctccact ccggcatccc cggcacggaa   2040

ggctggatgg cgcccgagct tctgcagctc ctgccaccag acagtcctac cagcgctgtg   2100

gacatcttct ctgcaggctg cgtgttctac tacgtgcttt ctggtggcag ccaccccttt   2160

ggagacagtc tttatcgcca ggcaaacatc ctcacagggg ctccctgtct ggctcacctg   2220

gaggaagagg tccacgacaa ggtggttgcc cgggacctgg ttggagccat gttgagccca   2280

ctgccgcagc cacgcccctc tgccccccag gtgctggccc acccccttctt ttggagcaga   2340

gccaagcaac tccagttctt ccaggacgtc agtgactggc tggagaagga gtccgagcag   2400

gagcccctgg tgagggcact ggaggcggga ggctgcgcag tggtccggga caactggcac   2460

gagcacatct ccatgccgct gcagacagat ctgagaaagt tccggtccta taaggggaca   2520

tcagtgcgag acctgctccg tgctgtgagg aacaagaagc accactacag ggagctccca   2580

gttgaggtgc gacaggcact cggccaagtc cctgatggct tcgtccagta cttcacaaac   2640

cgcttcccac ggctgctcct ccacacgcac cgagccatga ggagctgcgc ctctgagagc   2700

ctcttcctgc cctactaccc gccagactca gaggccagga ggccatgccc tggggccaca   2760

gggaggtga                                                           2769
```

<210> SEQ ID NO 9
<211> LENGTH: 922
<212> TYPE: PRT
<213> ORGANISM: homo sapiens
<220> FEATURE:
<221> NAME/KEY: VARIANT
<222> LOCATION: (1)...(922)
<223> OTHER INFORMATION: Xaa = Any Amino Acid

<400> SEQUENCE: 9

```
Met Arg Arg Ala Gly Ile Gly Glu Asp Ser Arg Leu Gly Leu Gln Ala
 1               5                  10                  15

Gln Pro Gly Ala Glu Pro Ser Pro Gly Arg Ala Gly Thr Glu Arg Ser
            20                  25                  30

Leu Gly Gly Thr Gln Gly Pro Gly Gln Pro Cys Ser Cys Pro Gly Ala
        35                  40                  45
```

-continued

```
Met Ala Ser Ala Val Arg Gly Ser Arg Pro Trp Pro Arg Leu Gly Leu
    50                  55                  60

Gln Leu Gln Phe Ala Ala Leu Leu Leu Gly Thr Leu Ser Pro Gln Val
65                  70                  75                  80

His Thr Leu Arg Pro Glu Asn Leu Leu Leu Val Ser Thr Leu Asp Gly
                85                  90                  95

Ser Leu His Ala Leu Ser Lys Gln Thr Gly Asp Leu Lys Trp Thr Leu
            100                 105                 110

Arg Asp Asp Pro Val Ile Glu Gly Pro Met Tyr Val Thr Glu Met Ala
        115                 120                 125

Phe Leu Ser Asp Pro Ala Asp Gly Ser Leu Tyr Ile Leu Gly Thr Gln
    130                 135                 140

Lys Gln Gln Gly Leu Met Lys Leu Pro Phe Thr Ile Pro Glu Leu Val
145                 150                 155                 160

His Ala Ser Pro Cys Arg Ser Ser Asp Gly Val Phe Tyr Thr Gly Arg
                165                 170                 175

Lys Gln Asp Ala Trp Phe Val Val Asp Pro Glu Ser Gly Glu Thr Gln
            180                 185                 190

Met Thr Leu Thr Thr Glu Gly Pro Ser Thr Pro Arg Leu Tyr Ile Gly
        195                 200                 205

Arg Thr Gln Tyr Thr Val Thr Met His Asp Pro Arg Ala Pro Ala Leu
    210                 215                 220

Arg Trp Asn Thr Thr Tyr Arg Arg Tyr Ser Ala Pro Pro Met Asp Gly
225                 230                 235                 240

Ser Pro Gly Lys Tyr Met Ser His Leu Ala Ser Cys Gly Met Gly Leu
                245                 250                 255

Leu Leu Thr Val Asp Pro Gly Ser Gly Thr Val Leu Trp Thr Gln Asp
            260                 265                 270

Leu Gly Val Pro Val Met Gly Val Tyr Thr Trp His Gln Asp Gly Leu
        275                 280                 285

Arg Gln Leu Pro His Leu Thr Leu Ala Arg Asp Thr Leu His Phe Leu
    290                 295                 300

Ala Leu Arg Trp Gly His Ile Arg Leu Pro Ala Ser Gly Pro Arg Asp
305                 310                 315                 320

Thr Ala Thr Leu Phe Ser Thr Leu Asp Thr Gln Leu Leu Met Thr Leu
                325                 330                 335

Tyr Val Gly Lys Asp Glu Thr Gly Phe Tyr Val Xaa Lys Ala Leu Val
            340                 345                 350

His Thr Gly Val Ala Leu Val Pro Arg Gly Leu Thr Leu Ala Pro Ala
        355                 360                 365

Asp Gly Pro Thr Thr Asp Glu Val Thr Leu Gln Val Ser Gly Glu Arg
    370                 375                 380

Glu Gly Ser Pro Ser Thr Ala Val Arg Tyr Pro Ser Gly Ser Val Ala
385                 390                 395                 400

Leu Pro Ser Gln Trp Leu Leu Ile Gly His His Glu Leu Pro Pro Val
                405                 410                 415

Leu His Thr Thr Met Leu Arg Val His Pro Thr Leu Gly Ser Gly Thr
            420                 425                 430

Ala Glu Thr Arg Pro Pro Glu Asn Thr Gln Ala Pro Ala Phe Phe Leu
        435                 440                 445

Glu Gln Gln Pro Gln Val Val Glu Lys Gln Gln Glu Thr Pro Leu Ala
    450                 455                 460

Pro Ala Asp Phe Ala His Ile Ser Gln Asp Ala Gln Ser Leu His Ser
```

```
465                 470                 475                 480

Gly Ala Ser Arg Arg Ser Gln Lys Arg Leu Gln Ser Pro Ser Lys Gln
                485                 490                 495

Ala Gln Pro Leu Asp Asp Pro Glu Ala Glu Gln Leu Thr Val Val Gly
            500                 505                 510

Lys Ile Ser Phe Asn Pro Lys Asp Val Leu Gly Arg Gly Ala Gly Gly
        515                 520                 525

Thr Phe Val Phe Arg Gly Gln Phe Glu Gly Arg Ala Val Ala Val Lys
    530                 535                 540

Arg Leu Leu Arg Glu Cys Phe Gly Leu Val Arg Arg Glu Val Gln Leu
545                 550                 555                 560

Leu Gln Glu Ser Asp Arg His Pro Asn Val Leu Arg Tyr Phe Cys Thr
                565                 570                 575

Glu Arg Gly Pro Gln Phe His Tyr Ile Ala Leu Glu Leu Cys Arg Ala
            580                 585                 590

Ser Leu Gln Glu Tyr Val Glu Asn Pro Asp Leu Asp Arg Gly Gly Leu
        595                 600                 605

Glu Pro Glu Val Val Leu Gln Gln Leu Met Ser Gly Leu Ala His Leu
    610                 615                 620

His Ser Leu His Ile Val His Arg Asp Leu Lys Pro Gly Asn Ile Leu
625                 630                 635                 640

Ile Thr Gly Pro Asp Ser Gln Gly Leu Gly Arg Val Val Leu Ser Asp
                645                 650                 655

Phe Gly Leu Cys Lys Lys Leu Pro Ala Gly Arg Cys Ser Phe Ser Leu
            660                 665                 670

His Ser Gly Ile Pro Gly Thr Glu Gly Trp Met Ala Pro Glu Leu Leu
        675                 680                 685

Gln Leu Leu Pro Pro Asp Ser Pro Thr Ser Ala Val Asp Ile Phe Ser
    690                 695                 700

Ala Gly Cys Val Phe Tyr Tyr Val Leu Ser Gly Gly Ser His Pro Phe
705                 710                 715                 720

Gly Asp Ser Leu Tyr Arg Gln Ala Asn Ile Leu Thr Gly Ala Pro Cys
                725                 730                 735

Leu Ala His Leu Glu Glu Glu Val His Asp Lys Val Val Ala Arg Asp
            740                 745                 750

Leu Val Gly Ala Met Leu Ser Pro Leu Pro Gln Pro Arg Pro Ser Ala
        755                 760                 765

Pro Gln Val Leu Ala His Pro Phe Phe Trp Ser Arg Ala Lys Gln Leu
    770                 775                 780

Gln Phe Phe Gln Asp Val Ser Asp Trp Leu Glu Lys Glu Ser Glu Gln
785                 790                 795                 800

Glu Pro Leu Val Arg Ala Leu Glu Ala Gly Gly Cys Ala Val Val Arg
                805                 810                 815

Asp Asn Trp His Glu His Ile Ser Met Pro Leu Gln Thr Asp Leu Arg
            820                 825                 830

Lys Phe Arg Ser Tyr Lys Gly Thr Ser Val Arg Asp Leu Leu Arg Ala
        835                 840                 845

Val Arg Asn Lys Lys His His Tyr Arg Glu Leu Pro Val Glu Val Arg
    850                 855                 860

Gln Ala Leu Gly Gln Val Pro Asp Gly Phe Val Gln Tyr Phe Thr Asn
865                 870                 875                 880

Arg Phe Pro Arg Leu Leu Leu His Thr His Arg Ala Met Arg Ser Cys
                885                 890                 895
```

-continued

```
Ala Ser Glu Ser Leu Phe Leu Pro Tyr Tyr Pro Pro Asp Ser Glu Ala
            900                 905                 910

Arg Arg Pro Cys Pro Gly Ala Thr Gly Arg
        915                 920
```

<210> SEQ ID NO 10
<211> LENGTH: 768
<212> TYPE: DNA
<213> ORGANISM: homo sapiens

<400> SEQUENCE: 10

```
atgagaaggg cggggatcgg cgaggactcc aggctggggt tgcaggccca gccaggggcg      60

gagccttctc cgggtcgggc ggggacagag cgctcccttg gaggcaccca gggacctggc     120

cagccgtgca gctgcccagg cgctatggcg agtgcggtca gggggtcgag gccgtggccc     180

cggctggggc tccagctcca gttcgcggcg ctgctgctcg ggacgctgag tccacaggtt     240

catactctca ggccagagaa cctcctgctg gtgtccacct tggatggaag tctccacgca     300

ctaagcaagc agacagggga cctgaagtgg actctgaggg atgatcccgt catcgaagga     360

ccaatgtacg tcacagaaat ggcctttctc tctgacccag cagatggcag cctgtacatc     420

ttggggaccc aaaaacaaca gggattaatg aaactgccat tcaccatccc tgagctggtt     480

catgcctctc cctgccgcag ctctgatggg gtcttctaca caggccggaa gcaggatgcc     540

tggtttgtgg tggaccctga gtcaggggag acccagatga cactgaccac agagggtccc     600

tccacccccc gcctctacat tggccgaaca cagtatacgg tcaccatgca tgacccaaga     660

gccccagccc tgcgctggaa caccacctac cgccgctact cagcgccccc catggatggc     720

tcacctggga aatataaccc tccatgtgat ctccacacac cagactga                  768
```

<210> SEQ ID NO 11
<211> LENGTH: 255
<212> TYPE: PRT
<213> ORGANISM: homo sapiens

<400> SEQUENCE: 11

```
Met Arg Arg Ala Gly Ile Gly Glu Asp Ser Arg Leu Gly Leu Gln Ala
 1               5                  10                  15

Gln Pro Gly Ala Glu Pro Ser Pro Gly Arg Ala Gly Thr Glu Arg Ser
            20                  25                  30

Leu Gly Gly Thr Gln Gly Pro Gly Gln Pro Cys Ser Cys Pro Gly Ala
        35                  40                  45

Met Ala Ser Ala Val Arg Gly Ser Arg Pro Trp Pro Arg Leu Gly Leu
    50                  55                  60

Gln Leu Gln Phe Ala Ala Leu Leu Leu Gly Thr Leu Ser Pro Gln Val
65                  70                  75                  80

His Thr Leu Arg Pro Glu Asn Leu Leu Leu Val Ser Thr Leu Asp Gly
                85                  90                  95

Ser Leu His Ala Leu Ser Lys Gln Thr Gly Asp Leu Lys Trp Thr Leu
            100                 105                 110

Arg Asp Asp Pro Val Ile Glu Gly Pro Met Tyr Val Thr Glu Met Ala
        115                 120                 125

Phe Leu Ser Asp Pro Ala Asp Gly Ser Leu Tyr Ile Leu Gly Thr Gln
    130                 135                 140

Lys Gln Gln Gly Leu Met Lys Leu Pro Phe Thr Ile Pro Glu Leu Val
145                 150                 155                 160
```

-continued

```
His Ala Ser Pro Cys Arg Ser Ser Asp Gly Val Phe Tyr Thr Gly Arg
                165                 170                 175

Lys Gln Asp Ala Trp Phe Val Val Asp Pro Glu Ser Gly Glu Thr Gln
            180                 185                 190

Met Thr Leu Thr Thr Glu Gly Pro Ser Thr Pro Arg Leu Tyr Ile Gly
        195                 200                 205

Arg Thr Gln Tyr Thr Val Thr Met His Asp Pro Arg Ala Pro Ala Leu
    210                 215                 220

Arg Trp Asn Thr Thr Tyr Arg Arg Tyr Ser Ala Pro Pro Met Asp Gly
225                 230                 235                 240

Ser Pro Gly Lys Tyr Asn Pro Pro Cys Asp Leu His Thr Pro Asp
                245                 250                 255
```